(12) United States Patent
Chen

(10) Patent No.: US 8,431,552 B2
(45) Date of Patent: Apr. 30, 2013

(54) COMPOSITION FOR TREATING METABOLIC SYNDROME

(76) Inventor: Chien-Hung Chen, Forest Hills, NY (US)

(*) Notice: Subject to any disclaimer, the term of this patent is extended or adjusted under 35 U.S.C. 154(b) by 294 days.

(21) Appl. No.: 12/014,932

(22) Filed: Jan. 16, 2008

(65) Prior Publication Data

US 2008/0176822 A1    Jul. 24, 2008

Related U.S. Application Data

(60) Provisional application No. 60/885,212, filed on Jan. 16, 2007.

(51) Int. Cl.
| | |
|---|---|
| A01N 37/36 | (2006.01) |
| A01N 43/38 | (2006.01) |
| A01N 37/52 | (2006.01) |
| A61K 31/405 | (2006.01) |
| A61K 31/155 | (2006.01) |

(52) U.S. Cl.
USPC ............................. 514/165; 514/415; 514/635

(58) Field of Classification Search .................. None
See application file for complete search history.

(56) References Cited

U.S. PATENT DOCUMENTS

| | | | |
|---|---|---|---|
| 5,100,919 A | 3/1992 | Ulrich | |
| 5,385,915 A | 1/1995 | Buxbaum | |
| 5,721,345 A | 2/1998 | Roberfroid et al. | |
| 5,840,719 A | 11/1998 | Rubin | |
| 6,589,944 B1 | 7/2003 | Rahbar | |
| 6,927,223 B1 | 8/2005 | Meadows | |
| 7,329,638 B2 | 2/2008 | Yang | |
| 2002/0040063 A1* | 4/2002 | Chandran et al. | 514/635 |
| 2002/0045621 A1 | 4/2002 | Reiner | |
| 2002/0137787 A1* | 9/2002 | Geho et al. | 514/415 |
| 2002/0173511 A1* | 11/2002 | Wurtman et al. | 514/252.12 |
| 2004/0053900 A1 | 3/2004 | Masferrer | |
| 2004/0132758 A1 | 7/2004 | Vaccaro et al. | |
| 2004/0167114 A1 | 8/2004 | Fliss | |
| 2005/0054731 A1 | 3/2005 | Folli et al. | |
| 2005/0080074 A1 | 4/2005 | Wacker et al. | |
| 2005/0187267 A1 | 8/2005 | Hamann | |
| 2006/0040980 A1 | 2/2006 | Lind | |
| 2006/0069161 A1 | 3/2006 | Lee et al. | |
| 2006/0134206 A1 | 6/2006 | Lyer et al. | |
| 2006/0147947 A1 | 7/2006 | Apfeld et al. | |
| 2006/0276416 A1 | 12/2006 | Sinclair et al. | |
| 2007/0015839 A1* | 1/2007 | Folli et al. | 514/635 |
| 2007/0105790 A1 | 5/2007 | Khodadoust | |
| 2007/0142291 A1 | 6/2007 | Lin | |
| 2007/0149466 A1 | 6/2007 | Milburn | |
| 2007/0161543 A1 | 7/2007 | Yu | |
| 2007/0191351 A1 | 8/2007 | Cowen | |
| 2007/0249583 A1 | 10/2007 | Stein | |
| 2009/0286760 A1 | 11/2009 | Chen | |

FOREIGN PATENT DOCUMENTS

| | | |
|---|---|---|
| WO | 01/82926 | 11/2001 |
| WO | WO 2004/078113 | 9/2004 |
| WO | 2005/023202 | 3/2005 |
| WO | WO 2005/025673 A1 | 3/2005 |
| WO | 2006/078698 | 7/2006 |
| WO | 2006/024491 | 3/2009 |
| WO | 2007/080124 | 7/2009 |

OTHER PUBLICATIONS

Fonseca: Clinical Cornerstone, 7(2/3):61-72, 2005.*
Muldoon et al. : J Clin. Endocrinology & Metabolism, 89(1):266-271, 2004.*
Prete et al. (Physiology & Behavior, 67 (5): 685-689, 1999).*
Beckman, "*Great Balls of Fat*", Science, Mar. 3, 2006, vol. 311.
Buhl, et al, "*Long-Term AICAR Administration Reducese Metabolic Distrubances and Lowers Blood Pressure in Rats Displaying Features of the Insulin Resistance Syndrome*", Diabetes, vol. 51, Jul. 2002.
Daval, et al, "*Anti-lipolytic Action of AMP-activated protein Kinase in Rodent Adipocytes*", The Journal of Biological Chemistry, vol. 280, No. 28, Issue of Jul. 1, pp. 25250-25257, 2005.
He, et al, "*Calyculin and okadaic acid promote perilipin phosphorylation and increae lipolysis in primary rat adipocytes*", Biochimica et Biophysica Acta 1761 (2006) 247-255.
Kemp, et al, "*AMP-activated protein kinase, super metabolic regulator*", 2003 Biochemical Society, pp. 162-168.
Knowler, et al, "*Reduction in the Incidence of Type 2 Diabetes with Lifestyle Intervention or Metformin*", N Engl J. Med, vol. 346, No. 6: Feb. 7, 2002: 393-403.
Merrill, et al, "*Influence of malonyl-CoA and palmitate concentration on rate of palmitate oxidation in rate muscle*", J. App Physiol. Nov. 1998; 85(5):1909-14.
Ruderman, et al,*Amp Kinase and Malonyl-COA: Targets for Therapy of the Metabolic Syndrome*, Nat. Rev. Drug Discovery, vol. 3, Apr. 2004, 340-51.
Saha, et al, "*Activation of Malonyl-CoA Decarboxylase in Rat Skeletal Muscle by Contraction and the AMP-activated Protein Kinase Activator 5-Aminoimidazole-4-carboxamide-1-β-d-ribofuranoside*", J. Bio. Chem, vol. 275, No. 32, Issue of Aug. 11, pp. 24279-24283, 2000.
Zhang, et al, "*Tumor Necrosis Factor-α Stimulates Lipolysis in Differentiated Human Adipocytes Through Activation of Extraceullar Signal-Related Kinase and Elevation of Intraceullar cAMP*," Diabetes, vol. 51, Oct. 2002.
Zhou, et al, "*Role of AMP-activated protein kinase in mechanism of metformin action*", The Journal of Clinical Investigation, vol. 108, No. 8, Oct. 2001: 1167-1174.
International Bureau, PCT International Preliminary Report on Patentability by the PCT International Bureau on PCT Application Serial No. PCT/US2009/044362, Nov. 25, 2010.
Barnes Christopher J. et al.: "Asprin, but not sodium salieylate, indomethacin, or nabumetone, reversibly suppresses 1,2-dimethylhydrazine-induced colonic aberrant crypt foci in rats", Digestive Diseases and Sciences, vol. 42, No. 5, 1997, pp. 920-926, ISSN: 0163-2116 (abstract only).
Fonesca: Clinical cornerstone, 7(2/3):61:72, 2005.

(Continued)

Primary Examiner — Bong-Sook Baek
(74) Attorney, Agent, or Firm — Fish Richardson P.C.

(57) ABSTRACT

The invention relates to a composition that includes a first agent selected from the group consisting of an oxidative phosphorylation inhibitor, an ionophore, and an adenosine 5'-monophosphate-activated Protein kinase (AMPK) activator; a second agent that possesses anti-inflammatory activity; and a third agent that possesses serotonin activity.

18 Claims, No Drawings

OTHER PUBLICATIONS

Greco et al. "Leptin regulates Tau phosphorylation and Amyloid through AMPK in Neuronal Cells", Biochem Biophys Res Commun., Feb. 27, 2009; vol. 380(1): 98-104.

Muldoon, et al.: J. Clin. Endocrinology & Metabolism, 89(1):266-271, 2004.

Sudlow et al. "Cyclic AMP Levels, Adenylyl Cyclase Activity, and Their Stimulation by Serotonin Quantified in Intact Neurons", J Gen Physiol, 1997, vol. 110(3), pp. 243-255; p. 244, col. 1, last para:5-HT (serotonin creatinine sulfate complex; Sigma Chemical Co.).

Suzuki Kaon et al.: "Metformin suppresses the colorectal carcinogenesis via activating AMP protein kinase in the mouse model", Gastroenterology, vol. 134, No. 4, Suppl. 1, Apr. 2008, p. A630 (abstract only).

Yu H -G et al. "The effects of acetylsalicylic acid on proliferation, apoptosis, and invasion of cyclooxygenase-2 negative colon cancer cells", European Journal of Clinical Investigation, vol. 32, No. 11, Nov. 2002, pp. 838-846 (abstract only).

Zakikhani Mahvash et al. "Metformin is an AMP kinase-dependent growth inhibitor for breast cancer cells", Cancer Research, vol. 66, No. 21, Nov. 2006, pp. 10269-10273.

Krejs, G.J., "Metabolic Benefits Associated with Sibutramine Therapy," Int. J. Obesity 26 (Suppl. 4): 534-537 (2002).

Jensen, M.D., "Potential Role of New Therapies in Modifying Cardiovascular Risk in Overweight Patients with Cardiovascular Risk Factors," Obesity 14 (Suppl. 3): 143S-149S, (2006).

Carruba, M.O. et al., "Effects of Dextrofenfluramine and Other Anorectic Drugs on Experimentally Induced Hyperphagias," Adv. Biosci. 60: 353-360 (1986).

Dowling et al., "Metformin Inhibits Mammalian Target of Rapamycin-Dependent Translation Initiation in Breast Cancer Cells", Cancer Res, 67: 10804-10812, Nov. 15, 2007.

Extended Search Report issued on Oct. 14, 2009 in European Application No. 09160525.3.

Harris et al., "Chemoprevention of Breast Cancer in Rats by Celecoxib, a Cyclooxygenase 2 Inhibitor", Cancer Research, 60, 2101-2103, Apr. 15, 2000.

International Preliminary Report on Patentability issued in international application PCT/US2008/051123 mailed on Jul. 30, 2009.

International Preliminary Report on Patentability issued from International Application No. PCT/US2009/044362 mailed on Nov. 25, 2010.

International Search Report and Written Opinion from International Application No. PCT/US10/27330 mailed May 6, 2010.

C.J. Glueck et al, "Metformin reduces weight, centripetal obesity, insulin, leptin, and low-density lipoprotein cholesterol in nondiabetic, morbidly obese subjects with body mass index greater than 30", Metabolism, vol. 50, No. 7, Jul. 1, 2001, pp. 856-861.

Pollock J. D, et al, "Peripherally administered serotonin decreases food intake in rats", Harmacology Biochemistry and Behavior, Elsevier, US, vol. 15, No. 2, Aug. 1, 1981, pp. 179-183.

Yuan M. et al, "Reversal of obesity-and-diet-induced insulin resistance with salicylates or targeted disruption of Ikkbeta", Science, American Association for the Advancement of Science, Washington, DC, US, vol. 293, No. 5535, Aug. 31, 2001, pp. 1673-1677.

* cited by examiner

COMPOSITION FOR TREATING METABOLIC SYNDROME

CROSS-REFERENCE TO RELATED APPLICATION

This application claims the benefit of U.S. Provisional Application 60/885,212, filed Jan. 16, 2007, the content of which is incorporated herein by reference in its entirety.

BACKGROUND

Metabolic syndrome is characterized by a group of metabolic risk factors, including abdominal obesity, atherogenic dyslipidemia (e.g., high triglyceride levels, low HDL cholesterol levels, and high LDL cholesterol levels), hypertension, insulin resistance, prothrombotic state (e.g., high fibrinogen or plasminogen activator inhibitor-1 levels), and proinflammatory state (e.g., elevated C-reactive protein levels). Metabolic syndrome has become increasingly common in the United States. It is estimated that over 50 million Americans have this disorder. There is a need to develop novel drugs to effectively treat this disorder.

SUMMARY

This invention is based on the unexpected discovery that a combination of certain known drugs exhibits synergistic effects in treating metabolic syndrome and various other diseases.

In one aspect, the invention features a composition that includes a first agent that can be an oxidative phosphorylation inhibitor, an ionophore, or an adenosine 5'-monophosphate-activated Protein kinase (AMPK) activator, a second agent that possesses anti-inflammatory activity, and a third agent that possesses or maintains serotonin activity. The term "oxidative phosphorylation inhibitor" refers to any suitable agents that inhibit oxidative phosphorylation, such as oxidative phosphorylation uncouplers. An ionophore is a lipid-soluble molecule capable of transporting an ion across the lipid bilayer of cell membranes; and an AMPK activator is an agent that activates AMPK to phosphorylate its substrates, e.g., acetyl-CoA carboxylase and malonyl-CoA decarboxylase. Examples of the first agent include metformin (e.g., metformin chloride), phenformin, buformin, ephedrine, thyroxine, salicylanilide, and salicylic acid. The second agent can be any suitable anti-inflammatory compounds (e.g., non-steroidal anti-inflammatory compounds). Examples include aspirin, diclofenac (e.g., diclofenac potassium or diclofenac sodium), ibuprofen (e.g., dexibuprofen or dexibuprofen lysine), indomethacin, acetaminophen, nimesulide, and a COX-2 inhibitor (e.g., a nitric oxide-based COX-2 inhibitor). The third agent can be a compound possessing or maintaining at least one of the serotonin's activities and, when used in combination with the first and second agents, effectively treats one or more the target diseases of this invention. Examples includes serotonin (e.g., serotonin sulfate, a serotonin creatinine sulfate complex, or serotonin hydrochloride) and a serotonin re-uptake inhibitor. A preferred composition contains metformin hydrochloride, aspirin, and a serotonin creatinine sulfate complex. The three agents mentioned above can treat the target diseases via biological mechanisms other than those described therein. For example, metformin may treat a target disease (e.g., diabetes) via a mechanism other than inhibiting oxidative phosphorylation or activating AMPK.

In another aspect, the invention features a composition consisting essentially of a first agent that can be an oxidative phosphorylation inhibitor, an ionophore, or an AMPK activator, a second agent that possesses anti-inflammatory activity, and a third agent that possesses serotonin activity. The term "consisting essentially of" used herein limits a composition to the three specified agents and those that do not materially affect its basic and novel characteristics, i.e., the efficacy in treating a target disease described herein. An example of such a composition contains the above-mentioned three agents and a pharmaceutically acceptable carrier.

The compositions described above can contain 5-5,000 mg (e.g., 5-3,000 mg, 5-1,500 mg or 5-1,000 mg) of the first agent, 1-5,000 mg (e.g., 1-3000 mg, 1-1,000 mg, 1-500 mg, or 1-100 mg) of the second agent, and 0.1-1,000 mg (e.g., 0.1-100 mg, 0.1-50 mg, or 0.1-30 mg) of the third agent, or in quantities of the same ratio as that calculated based on the above amounts.

In still another aspect, this invention features a method for treating metabolic syndrome, Parkinson's disease, or polycystic ovarian syndrome. The method includes administering to a subject in need thereof an effective amount of one or more of the compositions described above. The diseases mentioned above also include their associated disorders. For example, disorders associated with metabolic syndrome include atherosclerosis, coronary heart disease, stroke, obesity, diabetes, atherogenic dyslipidemia (e.g., high triglyceride levels, low HDL cholesterol levels, and high LDL cholesterol levels), hypertension, insulin resistance, prothrombotic state (e.g., high fibrinogen or plasminogen activator inhibitor-1 levels), and proinflammatory state (e.g., elevated C-reactive protein levels).

The term "treating" or "treatment" used herein refers to administering one or more above-described compositions to a subject, who has a disease described above, a symptom of such a disease, or a predisposition toward such a disease, with the purpose to confer a therapeutic effect, e.g., to cure, relieve, alter, affect, ameliorate, or prevent the disease, the symptom of it, or the predisposition toward it.

The composition described above can be in dry form (e.g., powder or tablet) or in aqueous form (e.g., beverage or syrup). It can be a dietary supplement or a pharmaceutical formulation (containing a pharmaceutically acceptable carrier). It can also be a drink or a food product. Examples include tea (e.g., a tea drink and the contents of a tea bag), soft drinks, juice (e.g., a fruit extract and a juice drink), milk, coffee, cookies, cereals, chocolates, and snack bars.

The first, second, and third agents described above include active compounds, as well as their salts, prodrugs, and solvates, if applicable. A salt, for example, can be formed between an anion and a positively charged group (e.g., amino) on an agent. Suitable anions include chloride, bromide, iodide, sulfate, nitrate, phosphate, citrate, methanesulfonate, trifluoroacetate, acetate, chlorophenyoxyacetate, malate, tosylate, tartrate, fumarate, glutamate, glucuronate, lactate, glutarate, benzoate, embonate, glycolate, pamoate, aspartate, parachlorophenoxyisobutyrate, formate, succinate, cyclohexanecarboxylate, hexanoate, octonoate, decanoate, hexadecanoate, octodecanoate, benzenesulphonate, trimethoxybenzoate, paratoluenesulphonate, adamantanecarboxylate, glycoxylate, pyrrolidonecarboxylate, naphthalenesulphonate, 1-glucosephosphate, sulphite, dithionate, and maleate. Likewise, a salt can also be formed between a cation and a negatively charged group (e.g., carboxylate) on an agent. Suitable cations include sodium ion, potassium ion, magnesium ion, calcium ion, and an ammonium cation such as tetramethylammonium ion. The agents also include salts containing quaternary nitrogen atoms. Examples of prodrugs include esters and other pharmaceutically acceptable derivatives, which, upon administration to a subject, are capable of providing active compounds. A solvate refers to a complex formed between an active compound and a pharmaceutically acceptable solvent. Examples of pharmaceutically acceptable solvents include water, ethanol, isopropanol, ethyl acetate, acetic acid, and ethanolamine.

Also within the scope of this invention is one or more compositions described above for use in treating an above-described disease, and the use of such a composition for the manufacture of a medicament for the just-mentioned treatment.

The details of one or more embodiments of the invention are set forth in the description below. Other features, objects, and advantages of the invention will be apparent from the description and from the claims.

DETAILED DESCRIPTION

A composition of this invention can include three agents.

The first agent can include, in addition to those described above, 4,6-dinitro-o-cresol, uncoupling proteins (e.g., UCP1, UCP2, or UCP3), carbonyl cyanide p-(trifluoromethoxy)phenyl-hydrazone, carbonyl cyanide m-chlorophenyl-hydrazone, C5 gene products, dinitrophenol (e.g., 2,4-dinitrophenol), efrapeptin (A23871), guanethidine, chlorpromazine, amytal, secobarbital, rotenone, progesterone, antimycin A, naphthoquinone, 8-hydroxyquinoline, carbon monoxide, cyanides, azides (e.g., $NaN_3$), dicoumarin, bilirubin, bile pigment, ephedrine, hydrogen sulfide, tetraiodothyronine, quercetin, 2,4-bis(p-chloroanilino)pyrimidine, glyceraldehyde-3-phosphate dehydrogenase, oligomycin, tributyltin chloride, aurovertin, rutamycin, venturicidin, mercurials, dicyclohexylcarbdiimide, Dio-9, m-chlorophenyl-hydrazone mesoxalonitrile, ionomycin, calcium ionophores (e.g., A23187, NMDA, CA 1001, or enniatin B), compounds that increase the $Ca^{+2}$ concentration in mitochondria (e.g., atractyloside, bongkrekic acid, thapsigargin, amino acid neurotransmitters, glutamate, N-methyl-D-aspartic acid, carbachol, ionophores, inducers of potassium depolarization), apoptogens (i.e., compounds that induce apoptosis), valinomycin, gramicidin, nonactin, nigericin, lasalocid, and monensin. The first agent can be an AMPK activator (e.g., metfomin or phenformin, buformin, AICAR, thienopyridones, resveratrol, nootkatone, thiazole, or adiponectin)

The second agent can include steroidal anti-inflammatory drugs and non-steroidal anti-inflammatory drugs. Examples of steroidal anti-inflammatory drugs include glucocorticoids, hydrocortisone, cortisone, beclomethasone, dipropionate, betamethasone, dexamethasone, prednisone, methylprednisolone, triamcinolone, fluocinolone acetonide, fludrocortisone, and beclometasone propionate. Examples of non-steroidal anti-inflammatory drugs (NASIDs) include A183827, ABT963, aceclofenac, acemetacin, acetyl salicylic acid, AHR10037, alclofenac, alminoprofen, ampiroxicam, amtolmetin guacil, apazone, atliprofen methyl ester, AU8001, benoxaprofen, benzydamine flufenamate, bermoprofen, bezpiperylon, BF388, BF389, BIRL790, BMS347070, bromfenac, bucloxic acid, butibufen, BW755C, C53, C73, C85, carprofen, CBS1108, celecoxib, CHF2003, chlorobiphenyl, choline magnesium trisalicylate, CHX108, cimicoxib, cinnoxicam, clidanac, CLX1205, COX-2 inhibitors, CP331, CS502, CS706, D1367, darbufelone, deracoxib, dexketoprofen, DFP, DFU, diflunisal, DP155, DRF4367, E5110, E6087, eltenac, ER34122, esflurbiprofen, etoricoxib, F025, felbinac ethyl, fenbufen, fenclofenac, fenclozic acid, fenclozine, fenoprofen, fentiazac, feprazone, filenadol, flobufen, florifenine, flosulide, flubichin methanesulfonate, flufenamic acid, fluprofen, flurbiprofen, FPL62064, FR122047, FR123826, FR140423, FR188582, FS205397, furofenac, GR253035, GW406381, HAI105, HAI106, HCT2035, HCT6015, HGP12, HN3392, HP977, HX0835. HYAL AT2101, ibufenac, ibuproxam-beta-cyclodextrin, icodulinum, IDEA070, iguratimod, imrecoxib, indoprofen, IP751, isoxepac, isoxicam, KC764, ketoprofen, L652343, L745337, L748731, L752860, L761066, L768277, L776967, L783003, L784520, L791456, L804600, L818571, LAS33815, LAS34475, licofelone, LM 4108, lobuprofen, lornoxicam, lumiracoxib, mabuprofen, meclofenamic acid, meclofenamate sodium, mefenamic acid, meloxicam, mercaptoethylguanidine, mesoporphyrin, metoxibutropate, miroprofen, mofebutazone, mofezolac, MX1094, nabumetone, naproxen sodium, naproxen-sodium/metoclopramide, NCX1101, NCX284, NCX285, NCX4016, NCX4215, NCX530, niflumic acid, nitric oxide-based NSAIDs (NitroMed, Lexington, Mass.), nitrofenac, nitroflurbiprofen, nitronaproxen, NS398, ocimum sanctum oil, ONO3144, orpanoxin, oxaprozin, oxindanac, oxpinac, oxycodone/ibuprofen, oxyphenbutazone, P10294, P54, P8892, pamicogrel, parcetasal, parecoxib, PD138387, PD145246, PD164387, pelubiprofen, pemedolac, phenylbutazone, pirazolac, piroxicam, piroxicam beta-cyclodextrin, piroxicam pivalate, pirprofen, pranoprofen, resveratrol, R-ketoprofen, R-ketorolac, rofecoxib, RP66364, RU43526, RU54808, RWJ63556, S19812, S2474, S33516, salicylsalicylic acid, satigrel, SC236, SC57666, SC58125, SC58451, SFPP, SKF105809, SKF86002, sodium salicylate, sudoxicam, sulfasalazine, sulindac, suprofen, SVT2016, T3788, TA60, talmetacin, talniflumate, tazofelone, tebufelone, tenidap, tenoxican, tepoxalin, tiaprofenic acid, tilmacoxib, tilnoprofen arbamel, tinoridine, tiopinac, tioxaprofen, tolfenamic acid, tolmetin, triflusal, tropesin, TY10222, TY10246, TY10474, UR8962, ursolic acid, valdecoxib, WAY120739, WY28342, WY41770, ximoprofen, YS134, zaltoprofen, zidometacin, and zomepirac.

The third agent includes serotonin and its functional equivalents. The functional equivalents of serotonin include serotonin transporter inhibitors (e.g., paroxetine, fluoxetine, fenfluramine, fluvoxamine, sertraline, imipramine, and those disclosed in WO 03/00663), serotonin receptor 2c modulators (e.g., BVT933, DPCA37215, IK264, PNU22394, WAY161503, R-1065, YM348, and those disclosed in U.S. Pat. No. 3,914,250, WO 01/66548, WO 02/10169, WO 02/36596, WO 02/40456, and WO 02/40457, WO 02/44152, WO 02/48124, WO 02/51844, and WO 03/033479), serotonin reuptake inhibitors (e.g., arylpyrrolidine compounds, phenylpiperazine compounds, benzylpiperidine compounds, piperidine compounds, tricyclic gamma-carbolines duloxetine compounds, pyrazinoquinoxaline compounds, pyridoindole compounds, piperidyindole compounds, milnacipran, citalopram, sertraline metabolite demethylsertraline, norfluoxetine, citalopram metabolite desmethylcitalopram, escitalopram, d,l-fenfluramine, femoxetine, ifoxetine, cyanodothiepin, litoxetine, dapoxetine, nefazodone, cericlamine, trazodone, mirtazapine, fluoxetine, fluvoxamine, indalpine, indeloxazine, milnacipran, paroxetine, sertraline, sibutramine, zimeldine, trazodone hydrochloride, dexfenfluramine, and those in U.S. Pat. No. 6,365,633, WO 01/27060, and WO 01/162341), serotonin and noradrenaline reuptake inhibitors (e.g., venlafaxine, venlafaxine metabolite O-desmethylvenlafaxine, clomipramine, and clomipramine metabolite desmethylclomipramine), serotonin 1A receptor antagonists (e.g., arylpiperazine compounds, azaheterocyclylmethyl derivatives of heterocycle-fused benzodioxans, or buspirone), serotonin 2A receptor antagonists (e.g., MDL 100907 and fananserin), serotonin 2B or 2C receptor antagonists (e.g., pirazino(aza)indole compounds or serotonergic compounds), serotonin 6 receptor antagonists (e.g., 5-halo-tryptamine compounds), serotonin 7 receptor antagonists (e.g., 5-halo-tryptamine compounds or quinoline compounds), serotonin dopamine antagonists (e.g., olanzapine and ziperasidone), monoamine re-uptake inhibitors (e.g., amides), pyridazinone aldose reductase inhibitors (e.g., pyridazinone compounds), serotonergic agents, stimulants of serotonin receptors (e.g., ergoloid mesylate or pergolide mesylate), stimulants of serotonin synthesis (e.g., vitamin B1, vitamin B3, vitamin B6, biotin, S-adenosylmethionine, folic acid, ascorbic acid, magnesium, coenzyme Q10, or piracetam), or serotonin agonists (e.g., fenfluramine).

All of the compounds mentioned above are known drugs and are readily available to the public. Some of them can be purchased from chemical companies, such as Sigma-Aldrich, St. Louis, Mo. Regimens for administering these drug compounds are well known and, if necessary, can be easily re-established. Effective doses will vary, as recognized by those skilled in the art, depending on the type or degree of the disease to be treated; the subject's size, weight, age, and sex; the route of administration; the excipient usage; and the possible co-usage with other therapeutic treatment. The daily dose of the compositions described above can be 5-5,000 mg (e.g., 10-2,500 or 10-3,000 mg) of the first agent, 1-5,000 mg (e.g., 2-1,000 or 2-3,000 mg) of the second agent, and 0.1-1,000 mg (e.g., 1-50 mg) of the third agent.

One aspect of this invention features a method of administering an effective amount of one or more of the above-mentioned compositions to a subject for treating a disease described above. Such a subject can be identified by a health care professional based on results from any suitable diagnostic method. "An effective amount" refers to the amount of one or more compositions described above that is required to confer a therapeutic effect on a treated subject.

To practice the method of the present invention, one or more of the above-described compositions can be administered parenterally, orally, nasally, rectally, topically, or buccally. The term "parenteral" as used herein refers to subcutaneous, intracutaneous, intravenous, intrmuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art.

A composition for topical administration can be prepared in form of an ointment, a gel, a plaster, an emulsion, a lotion, a foam, a cream of a mixed phase or amphiphilic emulsion system (oil/water-water/oil mixed phase), a liposome, a transfersome, a paste, or a powder.

Any of the compositions described above can also be administered in the form of suppositories for rectal administration. It also can be designed such that the composition is released in the intestine. For example, the composition is confined in a solid sub-unit or a capsule compartment that have respectively a matrix or a wall or a closure comprising an enteric polymer which dissolves or disperses at the pH of the small or large intestine to release the drug substance in the intestine. Suitable such polymers have been described above, for example with reference to U.S. Pat. No. 5,705,189.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active thiophene compound. Examples of other carriers include colloidal silicon oxide, magnesium stearate, cellulose, sodium lauryl sulfate, and D&C Yellow #10.

The compositions described above can be preliminarily screened for their efficacy in treating above-described diseases by an in vitro assay and then confirmed by animal experiments (See Examples 1-4 below) and clinic trials. Other methods will also be apparent to those of ordinary skill in the art.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All of the publications cited herein are incorporated by reference in their entirety.

EXAMPLE 1

In vivo Assays on Anti-Obesity Effects

Each of 120 eight-week old Sprague-Dawly (SD) female rats and 100 eight-week old SD male rats was fed with an unlimited amount of food for 14 days. The food intake and weight change of each rat were measured daily. The food conversion rate of each rat was then calculated using the following equation:

$$R = 100 \times \Delta W/F_t \%$$

In this equation, R refers to the food conversion rate, ΔW refers to the weight change, and $F_t$ refers to daily food intake. 88 female rats and 77 male rats were then selected and assigned to 11 groups, each group having 8 female rats and 7 male rats. Each of the following 10 test compositions was dissolved in a 10% glucose aqueous solution and was administered subcutaneously to a group of rats daily for 28 days: (1) metformin chloride (hereinafter referred to as metfomin) 15 mg/kg, (2) a serotonin creatintine sulfate comlex (hereinafter referred to as serotonin) 0.25 mg/kg, (3) aspirin 4 mg/kg, (4) serotonin 0.25 mg/kg+aspirin 4 mg/kg, (5) metformin 15 mg/kg+aspirin 4 mg/kg, (6) metformin 15 mg/kg+serotonin 0.25 mg/kg, (7) metformin 5 mg/kg+aspirin 4 mg/kg+serotonin 0.25 mg/kg, (8) metformin 15 mg/kg+aspirin 4 mg/kg+serotonin 0.25 mg/kg, (9) metformin 45 mg/kg+aspirin 4 mg/kg+serotonin 0.25 mg/kg, and (10) sibutramine 2 mg/kg. The rats in the $11^{th}$ group were not administered with any drug and were used as a control group. The results show that rats administered with a combination of metformin, aspirin, and serotonin gained less weight than rats administered with each ingredient alone or any combination of two ingredients. Further, the average weight gain of the rats decreased as the daily dosage of metformin increased.

The total food intakes over 28 days were measured for all groups. The results show that the total food intakes of groups (1)-(10) were substantially the same that of control group (11). In other words, the test compositions did not significantly affect the appetite of the rats.

The food conversion rates were calculated for all groups. The results show that rats administered with a combination of metformin, aspirin, and serotonin could have a much lower food conversion rate than rats administered with each ingredient alone or any combination of two ingredients.

EXAMPLE 2

In vivo Assays on Antihypertensive Effects

60 SD male rats (90-110 g) were provided by Guang Dong Medical Laboratory Animal Center (FuoShan, Guang Dong, China). After each rat was anesthetized, a U-shaped silver clamp with an inner diameter of 0.2-0.25 mm was used to narrow kidney artery. 40 rats with good recovery two weeks after the surgery were selected and assigned to 5 group, each group having 8 rats. Each of the following 4 test compositions was dissolved in a 10% glucose aqueous solution and was administered to a group of rats daily for 9 weeks: (1) metformin 45 mg/kg+aspirin 4 mg/kg+serotonin 0.25 mg/kg, (2) metformin 15 mg/kg+aspirin 4 mg/kg+serotonin 0.25 mg/kg, (3) metformin 5 mg/kg+aspirin 4 mg/kg+serotonin 0.25 mg/kg, and (4) nitedipine 2 mg/kg. The rats in the $5^{th}$ group were administered with a 10% glucose aqueous solution only and were used as a control group. The test compositions were administered subcutaneously except for nitedipine, which was administered by gastric perfusion. The tail arterial pressure of each rat was measured at the end of the $5^{th}$ week and the $9^{th}$ week.

The results show that the blood pressure of the rats in group (1) at the end of the $5^{th}$ and $9^{th}$ weeks were significantly lowered than that of the rats in the control group (i.e., group (5)) and the group in which the rats were fed with nitedipine (i.e., group (4)).

EXAMPLE 3

In vivo Assays on Acute Antihypertensive Effects

Renovascular hypertensive rats were prepared as follows: A male SD rat (90-110 g) was anesthetized with pentobarbitol sodium (45 mg/kg). A U-shaped silver clamp with an inner diameter of 0.18 mm was used to narrow kidney artery. The blood pressure of the rat increased significantly after 3-6 weeks and stabilized after about 8 weeks. The rats having a systolic pressure of between 180-240 mmHg were used in the following steps.

The rats prepared above were assigned to 4 groups. Each of the following 3 test compositions were dissolved in a 10% glucose aqueous solution: (1) metformin 45 mg/kg+aspirin 4 mg/kg+serotonin 0.25 mg/kg, (2) metformin 15 mg/kg+aspirin 4 mg/kg+serotonin 0.25 mg/kg, and (3) metformin 5 mg/kg+aspirin 4 mg/kg+serotonin 0.25 mg/kg. The rats in the $4^{th}$ group were administered with a 10% glucose solution only and were used as a control group. Each rat was then anesthetized with pentobarbitol sodium (45 mg/kg) and affixed to a board. A tube was inserted into trachea to maintain the breathing of the rat. Another tube was then inserted to the neck artery to measure the blood pressure. The blood pressure was measured by using a BL-420E biological signal collecting and processing system. When the neck artery blood pressure of the rat was stabilized, a test composition or the 10% glucose aqueous solution was administered subcutaneously in the abdomen section. The neck artery blood pressure was measured at 15, 30, 45, 60, 90, 120, 150, 180, 210, and 240 minutes after administration.

The results show that the neck artery blood pressure of the rats in groups (1) and (2) started to decrease at 15 minutes and reached the lowest levels at 120-150 minutes. The average neck artery blood pressure values were lowered as much as 29.7±5.2 mmHg and 20.3±2.9 mmHg, respectively, compared to that measured before administration of the test composition. The neck artery blood pressure did not return to the level before administration of the test composition even after 4 hours. The results also show that the test composition did not significantly affect the heart rate of the rats.

EXAMPLE 4

In vivo Assay on Effects of Lowering Blood Glucose Levels

Male Sprague-Dawly (SD) rats (180-210 g) were intraperitoneally injected with streptozocin (50 mg/kg) to induce type 2 diabetes. Rats having blood glucose levels higher than 17 mmol/L after the injection were assigned randomly to five groups, each including 10 rats. The rats in each of the five groups were then treated with the three test compositions described in Example 3 above, i.e., metformin 45 mg/kg+aspirin 4 mg/kg+serotonin 0.2 mg/kg (high dose), metformin 15 mg/kg+aspirin 4 mg/kg+serotonin 0.2 mg/kg (medium dose), and metformin 5 mg/kg+aspirin 4 mg/kg+serotonin 0.2 mg/kg (low dose); metformin alone at the dosage of 0.135 g/kg (metformin); and a vehicle control (control). 10 normal male SD rats, serving as normal controls, were subjected to the same treatment.

The blood glucose level of each treated rat was measured before treatment and 3-hour, 6-hour, 3-day, 7-day, 14-day, and 21-day after treatment. Results thus obtained demonstrate that the three test compositions significantly lowered the blood glucose levels in the type 2 diabetic rats.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A composition, consisting essentially of:
   a first agent which is metformin or a salt thereof;
   a second agent which is aspirin or a salt thereof; and
   a third agent which is serotonin or a salt thereof.

2. The composition of claim 1, wherein the first agent is metformin or metformin hydrochloride.

3. The composition of claim 1, wherein the second agent is aspirin.

4. The composition of claim 1, wherein the third agent is serotonin sulfate, a serotonin creatinine sulfate complex, or serotonin hydrochloride.

5. The composition of claim 1, wherein a daily dose of the composition contains 5-5,000 mg of the first agent, 1-5,000 mg of the second agent, and 0.1-1000 mg of the third agent.

6. The composition of claim 5, wherein the daily dose of the composition contains 5-1,500 mg of the first agent, 1-1,000 mg of the second agent, and 0.1-100 mg of the third agent.

7. The composition of claim 6, wherein the daily dose of the composition contains 5-1,000 mg of the first agent, 1-500 mg of the second agent, and 0.1-50 mg of the third agent.

8. The composition of claim 1, wherein the composition consists essentially of metformin hydrochloride, aspirin, and a serotonin creatinine sulfate complex.

9. The composition of claim 8, wherein a daily dose of the composition contains 5-5,000 mg of metformin hydrochloride, 1-5,000 mg of aspirin, and 0.1-1,000 mg of the serotonin creatinine sulfate complex.

10. The composition of claim 9, wherein the daily dose of the composition contains 5-1,500 mg of metformin hydrochloride, 1-1,000 mg of aspirin, and 0.1-100 mg of the serotonin creatinine sulfate complex.

11. The composition of claim 10, wherein the daily dose of the composition contains 5-1,000 mg of metformin hydrochloride, 1-500 mg of aspirin, and 0.1-50 mg of the serotonin creatinine sulfate complex.

12. The composition of claim 1, wherein the composition further comprises a pharmaceutically acceptable carrier.

13. A method for treating metabolic syndrome, comprising administering to a subject in need thereof an effective amount of a composition consisting essentially of first, second, and third agents,
   wherein the first agent is metformin or a salt thereof; the second agent is aspirin or a salt thereof; and the third agent is serotonin or a salt thereof.

14. The method of claim 13, wherein the composition consists essentially of metformin hydrochloride, aspirin, and a serotonin creatinine sulfate complex.

15. A method for treating obesity, comprising administering to a subject in need thereof an effective amount of a composition consisting essentially of first, second, and third agents,
   wherein the first agent is metformin or a salt thereof; the second agent is aspirin or a salt thereof; and the third agent is serotonin or a salt thereof.

16. The method of claim 15, wherein the composition consists essentially of metformin hydrochloride, aspirin, and a serotonin creatinine sulfate complex.

17. A method for treating type 2 diabetes, comprising administering to a subject in need thereof an effective amount of a composition consisting essentially of first, second, and third agents,
   wherein the first agent is metformin or a salt thereof; the second agent is aspirin or a salt thereof; and the third agent is serotonin or a salt thereof.

18. The method of claim 17, wherein the composition consists essentially of metformin hydrochloride, aspirin, and a serotonin creatinine sulfate complex.

* * * * *

UNITED STATES PATENT AND TRADEMARK OFFICE
CERTIFICATE OF CORRECTION

PATENT NO. : 8,431,552 B2
APPLICATION NO. : 12/014932
DATED : April 30, 2013
INVENTOR(S) : Chien-Hung Chen It is certified that error appears in the above-identified patent and that said Letters Patent is hereby corrected as shown below:

Title page, column 2, Other Publications
Line 6, delete "*Reducese*" and insert -- *Reduces* --.

Title page, column 2, Other Publications
Line 7, delete "*Distrubances*" and insert -- *Disturbances* --.

Title page, column 2, Other Publications
Line 14, delete "*increae*" and insert -- *increase* --.

Title page, column 2, Other Publications
Line 22, delete "*rate muscle*" and insert -- *rat muscle* --.

Title page, column 2, Other Publications
Line 33, delete "*Extraceullar*" and insert -- *Extracellular* --.

Title page, column 2, Other Publications
Line 34, delete "*Intraceullar*" and insert -- *Intracellular* --.

Title page, column 2, Other Publications
Line 42, delete "Asprin," and insert -- Aspirin, --.

Title page, column 2, Other Publications
Line 42, delete "salieylate," and insert -- salicylate, --.

Title page, column 2, Other Publications
Line 47, delete "Fonesca:" and insert -- Fonseca: --.

Title page, column 2, Attorney, Agent, or Firm
Line 1, delete "Fish Richardson P.C." and insert -- Fish & Richardson P.C. --.

Signed and Sealed this
Twentieth Day of August, 2013

Teresa Stanek Rea
*Acting Director of the United States Patent and Trademark Office*

Title page 2, column 2, Other Publications
Line 21, delete "Harmacology" and insert -- Pharmacology --.